US007015485B2

(12) United States Patent
Kitagawa

(10) Patent No.: US 7,015,485 B2
(45) Date of Patent: Mar. 21, 2006

(54) LASER SCANNING MICROSCOPE, SEMICONDUCTOR LASER LIGHT SOURCE UNIT, SCANNING UNIT FOR A LASER SCANNING MICROSCOPE, AND METHOD OF CONNECTING SEMICONDUCTOR LIGHT SOURCE TO SCANNING MICROSCOPE

(75) Inventor: Junichi Kitagawa, Fuchu (JP)

(73) Assignee: Olympus Optical Co., Ltd., Tokyo (JP)

(*) Notice: Subject to any disclaimer, the term of this patent is extended or adjusted under 35 U.S.C. 154(b) by 202 days.

(21) Appl. No.: 10/602,361

(22) Filed: Jun. 23, 2003

(65) Prior Publication Data

US 2004/0061073 A1 Apr. 1, 2004

(30) Foreign Application Priority Data

Jun. 24, 2002 (JP) ............................ 2002-182798

(51) Int. Cl.
*G01N 21/64* (2006.01)

(52) U.S. Cl. .............................. 250/458.1; 250/459.1; 356/317; 356/318

(58) Field of Classification Search ............ 250/458.1, 250/459.1, 339.01, 339.02, 578.1, 230, 239, 250/339.06; 356/317, 318
See application file for complete search history.

(56) References Cited

U.S. PATENT DOCUMENTS 6,154,282 A 11/2000 Lilge et al.
6,167,173 A 12/2000 Schoeppe et al.
6,184,535 B1 * 2/2001 Kashima et al. ......... 250/459.1
6,423,956 B1 * 7/2002 Mandella et al. ........ 250/201.3
6,486,458 B1 11/2002 Schoeppe et al.
6,496,307 B1 * 12/2002 Engelhardt et al. ......... 359/389
6,690,511 B1 * 2/2004 Engelhardt et al. ......... 359/385
6,693,945 B1 * 2/2004 Shimada ...................... 372/98
6,844,963 B1 * 1/2005 Iketaki et al. ............... 359/368
6,903,816 B1 * 6/2005 Nakata et al. .............. 356/318
2001/0030800 A1 * 10/2001 Engelhardt et al. ......... 359/368
2001/0045523 A1 * 11/2001 Baer et al. ............... 250/459.1
2002/0030884 A1 * 3/2002 Engelhardt et al. ......... 359/385
2002/0181096 A1 * 12/2002 Sasaki ........................ 359/389
2003/0030807 A1 * 2/2003 Takahashi eat al. ......... 356/399
2003/0062484 A1 * 4/2003 Nakata et al. ........... 250/458.1
2003/0107732 A1 * 6/2003 Sasaki et al. ............... 356/318
2003/0197924 A1 * 10/2003 Nakata ....................... 359/368

FOREIGN PATENT DOCUMENTS

JP 11-231222 A 8/1999

* cited by examiner

*Primary Examiner*—David Porta
*Assistant Examiner*—Faye Polyzos
(74) *Attorney, Agent, or Firm*—Frishauf, Holtz, Goodman & Chick, P.C.

(57) ABSTRACT

A laser scanning microscope according to the present invention is a laser scanning microscope which scans a laser beam on a sample by a scanning optical system in a scanning optical system main body to detect a fluorescence or reflected light from the sample, and a light source section comprising a light source manufactured by a semiconductor process and an optical fiber provided on a radiation side of the light source is incorporated in the scanning optical system main body.

14 Claims, 4 Drawing Sheets

LASER SCANNING MICROSCOPE, SEMICONDUCTOR LASER LIGHT SOURCE UNIT, SCANNING UNIT FOR A LASER SCANNING MICROSCOPE, AND METHOD OF CONNECTING SEMICONDUCTOR LIGHT SOURCE TO SCANNING MICROSCOPE

CROSS-REFERENCE TO RELATED APPLICATIONS

This application is based upon and claims the benefit of priority from the prior Japanese Patent Application No. 2002-182798, filed Jun. 24, 2002, the entire contents of which are incorporated herein by reference.

BACKGROUND OF THE INVENTION

1. Field of the Invention

The present invention relates to a laser scanning microscope which scans a light flux from a light source, irradiates a sample with it and detects a fluorescence or reflected light from the sample, semiconductor laser light source unit, scanning unit for a laser scanning microscope, and a method of connecting a semiconductor light source to a scanning microscope.

2. Description of the Background Art

In recent years, development of a semiconductor light source has advanced, and wavelength bands of infrared/near infrared to red and blue can be covered. Based on this, in an apparatus using a laser as a light source, an effective use of a semiconductor laser has been demanded in order to enable a wavelength selection and a reduction in size of a light source and the apparatus. For example, U.S. Pat. No. 6,154,282 discloses a fluorescence microscope which utilizes a semiconductor light source.

FIG. 4 is a view showing a structure of a laser microscope disclosed in Jpn. Pat. Appln. KOKAI Publication No. 11-231222. In FIG. 4, a gas laser is used as a light source having a high brightness and the directivity. In FIG. 4, reference character A denotes a microscope unit and B designates a scanning head (scanning optical system main body).

The microscope unit A comprises a light source 101, an illumination lens 102, a beam splitter 103, an object lens 104, a sample 105, a condenser 106, a light source 107, a receiving device 108, a first body tube lens 109, a second body tube lens 110, a monitoring light beam path having an eyepiece lens 111, and a beam splitter 112 for combining the scanning light beams, and the light beam path can be switched by a swiveling mirror 114.

Laser modules 131 and 132 include lasers and are connected to the scanning head B through a visible light beam fibers 141 and 142. Coupling of the visible light beam fibers 141 and 142 is carried out by moving type collimator lenses 160 and 160 and light beam direction conversion elements 171 and 172.

In the scanning head B, a partial transmitting mirror 118 narrows down the monitoring light beam in a direction of a line path filter 151 and a monitor diode 119 on a neutral filter 150. The scanning unit consists of a scanning object lens 152, a scanner 153, a main beam splitter 154, and a common image forming lens 155 for detection channels 261 to 264. A direction conversion prism 157 reflects the light beam from the sample 105 in a direction of a dichroic beam splitter 158. A plurality of sets of a pin hole 159, a radiation filter 130 and a receiving element (PMT) 133 are arranged at the rear of the dichroic beam splitter 158.

The semiconductor laser radiates its outgoing beam with a spread based on its structure. Usually, this spread has a radiation characteristic which differs depending on horizontal/vertical directions, and optically has an astigmatic difference which is an aberration component. Therefore, in the arrangement of such an optical system having a regular spherical lens structure as disclosed in U.S. Pat. No. 6,154,282, the light source and the lens system cannot be efficiently optically combined with each other.

In case of using a technique which shapes the beam by using a cylindrical lens or a prism and leads it into the apparatus, the loss of the beam or the remanence of the astigmatic difference actually cannot be avoided.

Furthermore, as shown in FIG. 4, since a combined optical system using a laser light source and a plurality of lasers requires a very large space, it is set as an external light source different from the scanning head (scanning optical system main body) because of the structure of the apparatus.

BRIEF SUMMARY OF THE INVENTION

A laser scanning microscope according to the present invention is a laser scanning microscope which scans a laser beam on a sample by a scanning optical system in a scanning optical system main body to detect a fluorescence or reflected light from the sample, and a light source section comprising a light source manufactured by a semiconductor process and an optical fiber provided on a radiation side of the light source is incorporated in the scanning optical system main body.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Embodiments according to the present invention will now be described hereinafter with reference to the accompanying drawings.

Figure 1:
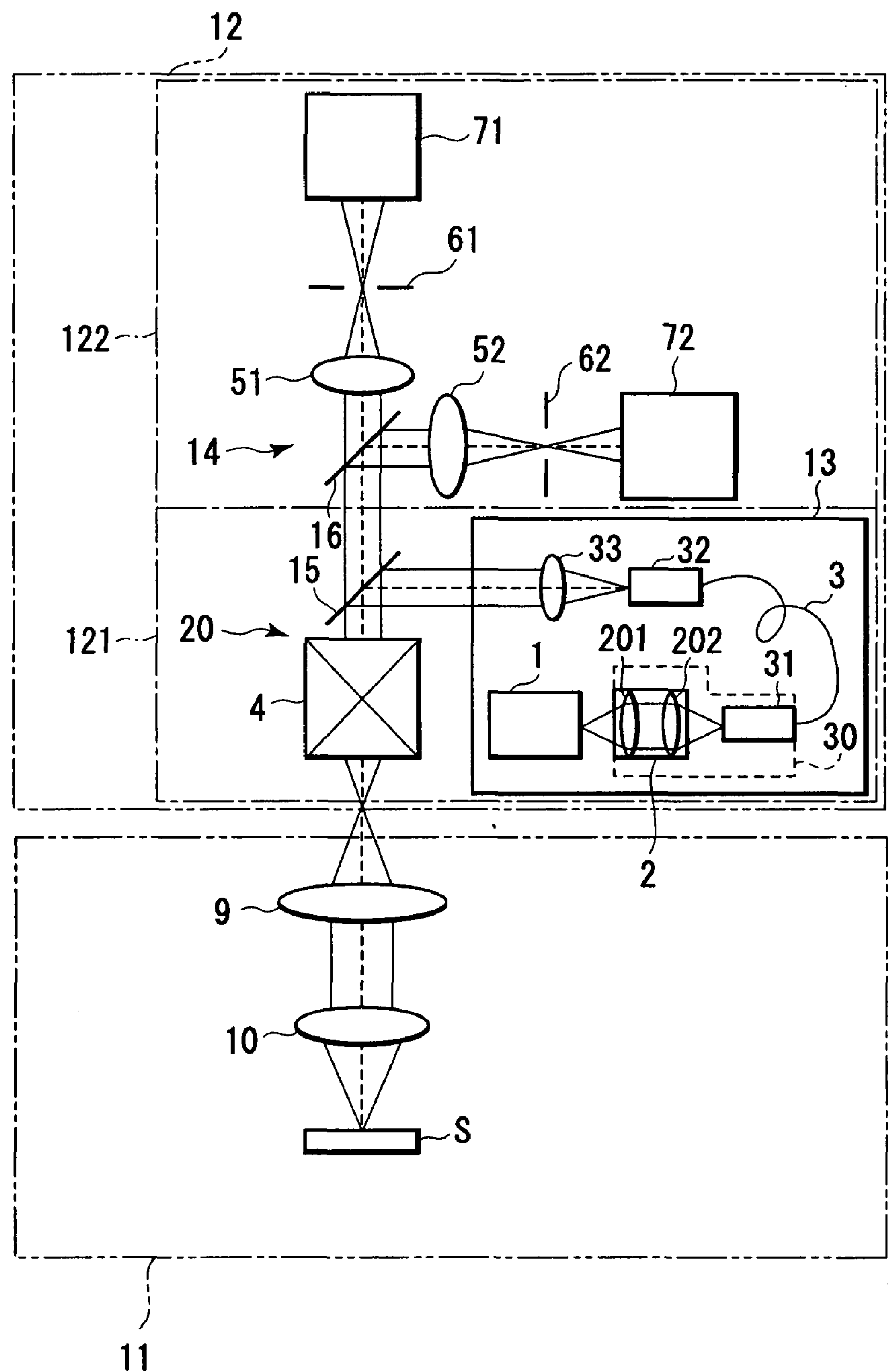
FIG. 1 is a view showing a structure of a two-channel detecting/laser scanning confocal microscope according to a first embodiment of the present invention.

FIG. 1 is a view showing a structure of a two-channel detecting/laser scanning confocal microscope according to the first embodiment of the present invention. The microscope shown in FIG. 1 comprises a microscope section 11 and a laser scanning/detecting system main body 12 (scanning optical system main body). The microscope section 11 and the laser scanning/detecting system main body 12 are configured by independent housings, respectively. When the laser scanning/detecting system main body 12 is attached to the microscope section 11, a laser scanning confocal microscope is configured.

The microscope section 11 includes an image forming lens 9 and an object lens 10 as a main optical system. The laser scanning/detecting system main body 12 has a scanning section 121 and a detection section 122. The scanning section 121 includes a light source section 13 and a scanning optical system 20 in one housing. The detection section 122 includes therein a detection optical system 14. It is to be noted that this embodiment has a structure including both the scanning section and the detection section in the scanning optical system main body, but only the scanning section may be provided in the scanning optical system main body and the detection section may be included in another housing. In this case, the light source section is included in the scanning section (scanning optical system main body).

The light source section 13 in the scanning section 121 comprises a semiconductor laser 1 (semiconductor laser diode: light source manufactured by a semiconductor process), a beam shaping section 2, a fiber incident optical system 31, an optical fiber 3, a fiber radiation optical system 32 and a lens 33. The beam shaping section 2 has a set of a spherical lenses 201 and 202. It is to be noted that the beam shaping section 2 and the fiber incident optical system 31 configure a shaping incident optical system 30. This shaping incident optical system 30 is an optical system which have functions of both the beam shaping section 2 and the fiber incident optical system 31. The shaping incident optical system 30 is disposed between the semiconductor laser 1 and the optical fiber 3. The conformation of the shaping incident optical system is enabled in another embodiment which will be described later. A scanner 4 in the scanning system 20 scans the light which is emitted from the light source section 13 and is reflected by a dichroic mirror 15. The detection optical system 14 in the detection section 122 comprises a dichroic mirror 16, confocal lenses 51 and 52, pin holes 61 and 62, and detectors 71 and 72.

In the light source section 13 of the scanning section 121, the laser beam which is emitted from the semiconductor laser 1 is condensed and shaped by the beam shaping section 2. The shaped beam is focused on an incident end surface of the optical fiber 3 by the fiber incident optical system 31, and caused to outgo to the dichroic mirror 15 through the optical fiber 3, the fiber radiation optical system 32 and the lens 33. The beam reflected in a direction of the scanner 4 by the dichroic mirror 15 is scanned by the scanner 4, and a sample S is irradiated with this beam through the image forming lens 9 and the object lens 10 in the microscope section 11.

The fluorescence or the reflected light from the sample S returns to the scanning section 121 of the laser scanning/detecting system main body 12 through the object lens 10 and the image forming lens 9. The fluorescence or the reflected light which has returned to the scanning section 121 is transmitted through the dichroic mirror 15 via the scanner 4, and caused to diverge by the dichroic mirror 16 of the detection section 122. The fluorescence or the reflected light which has been transmitted through the dichroic mirror 16 is led to the detector 71 through the confocal lens 51 and the pin hole 61. The fluorescence or the reflected light reflected by the dichroic mirror 16 is led to the detector 72 through the confocal lens 52 and the pin hole 62.

In the structure of FIG. 1, although the detection portion 122 forms a two-channel detection system, the basic structure is not changed even if a single detector or three or more detectors are used. In the light source portion 13, the light emitted from the semiconductor laser 1 is the divergent light having an astigmatic difference component, and the beam shaping section 2 collects and shapes this divergent light and efficiently combines it in the optical fiber 3 through the fiber incident optical system 31.

The beam shaping section 2 is configured by a cylindrical lens or a prism and a spherical lens system. Of course, if the astigmatic difference component is small, it can be configured by only the spherical lens system. The drawing shows an example using a set of spherical lenses 201 and 202 for the simplicity. It is to be noted that an example using a set of the spherical lenses in the beam shaping section is likewise illustrated in later-described second and third embodiments, but the above-described other method can be adopted.

As a result, the light source section 13 can be incorporated in the scanning section 121 of the laser scanning/detecting system main body 12, and the entire apparatus can sufficiently become compact. As shown in FIG. 1, since a radiation end of the optical fiber 3 serves as the light source of the entire apparatus, the light source section 13 can be freely arranged in a range of a length of the optical fiber 3.

Moreover, the astigmatic difference component can be eliminated from the beam outgoing from the optical fiber 3 by using the beam shaping section 2 and the optical fiber 3, and the beam can be processed as a sufficiently small ideal point light source. Further, in the laser scanning confocal microscope, the beam from the laser must be shaped as a point light source on a sample surface. If the light source has the aberration component, shaping of the point light source can be sufficiently carried out, which improves an image quality in the entire apparatus. In an apparatus using an optical system which excellently performs aberration correction in order to obtain a high resolution image like the laser scanning confocal microscope, a use of the semiconductor laser can contribute to a maintenance/improvement of the image quality and a reduction in size of the light source. Additionally, by using a polarization plane preserving single mode optical fiber as the optical fiber 3, the light outgoing from the optical fiber 3 can be matched with a polarization direction of the semiconductor laser 1, and the linear polarization characteristic of the semiconductor laser 1 can be maintained in the apparatus. Further, the microscope can be applied to differential interference observation as well as fluorescence observation in the laser scanning confocal microscope. Furthermore, since fluorescent molecules have the polarization characteristic, the microscope can be also used to detect this characteristic.

Figure 2:
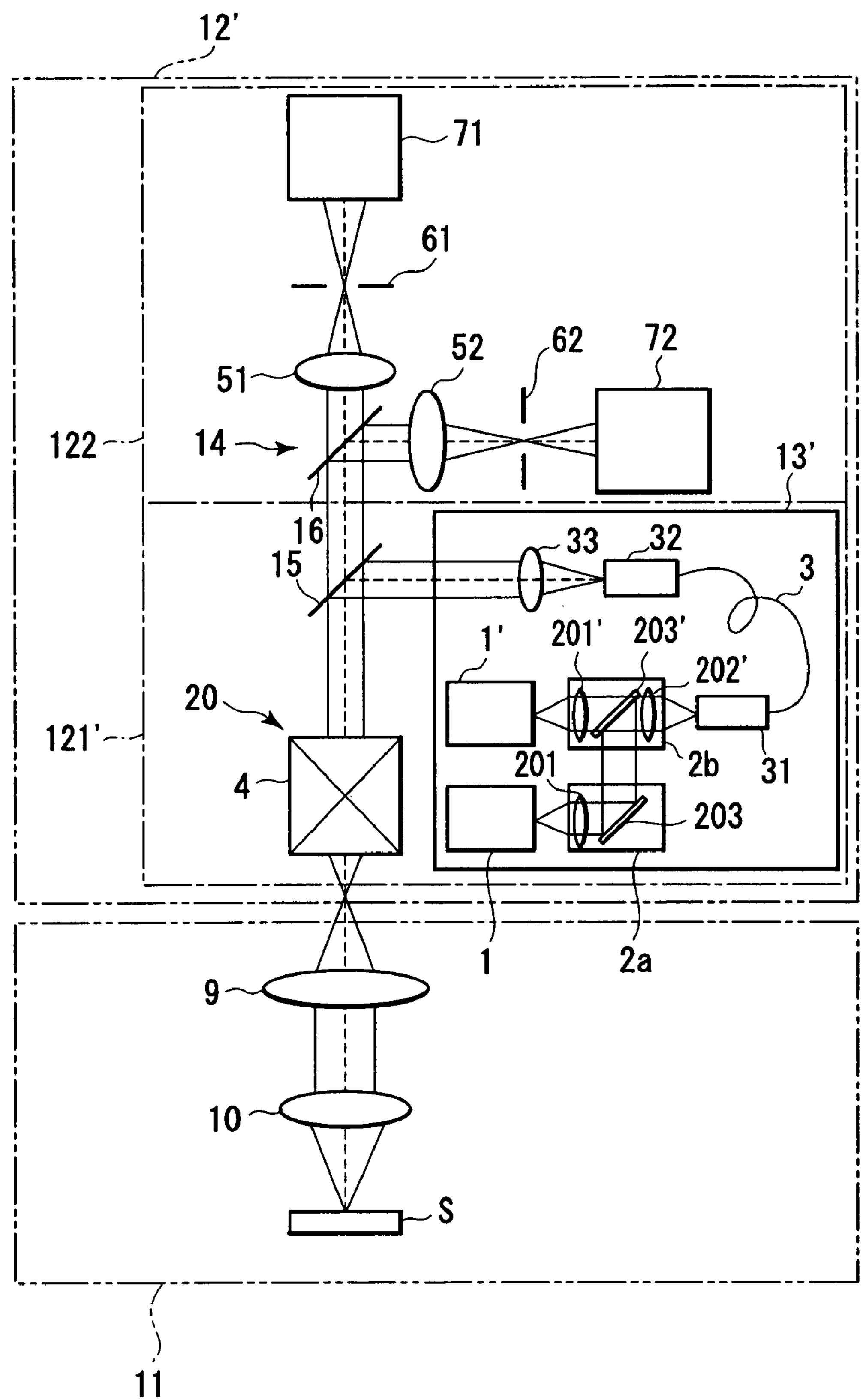
FIG. 2 is a view showing a structure of a two-channel detecting/laser scanning confocal microscope according to a second embodiment of the present invention.

FIG. 2 is a view showing a structure of a two-channel detecting/laser scanning confocal microscope according to a second embodiment of the present invention. In FIG. 2, like reference numerals denote parts equal to those in FIG. 1.

In an apparatus structure of FIG. 2, as parts different from the first embodiment, two types of semiconductor lasers 1 and 1' (semiconductor laser diodes: light sources manufactured by a semiconductor process) having different wavelengths are used as light sources of a light source section 13' in a scanning section 121' configuring a laser scanning/detecting system main body 12', and two beam shaping sections 2*a* and 2*b* are provided. The beam shaping section 2*a* has a spherical lens 201 and a deflection mirror 203. The beam shaping section 2*b* has a set of spherical lenses 201' and 202' and an optical member 203'.

If the semiconductor lasers 1 and 1' have different wavelengths, a dichroic mirror is used as an optical member 203'. This dichroic mirror has a characteristic of reflecting a wavelength of the light from the semiconductor laser 1 and transmitting a wavelength of the light from the semiconductor laser 1'. In case of equalizing the wavelengths of the semiconductor lasers 1 and 1' and improving the intensity of the light, a polarized beam splitter (PBS) is used as an optical member 203'. In this case, since the laser beam outputted from each of the semiconductor lasers 1 and 1' is the linear polarized light, polarization directions of the semiconductor lasers 1 and 1' are shifted 90 degrees so as to be orthogonal to each other, and the optical member 203' is arranged so as to reflect the emitted light from the semiconductor laser 1 and transmit the emitted light from the semiconductor laser 1' therethrough. A use of the two semiconductor lasers having the same wavelength is very effective in cases where the output intensity should be increased in order to irradiate a sample with the beam having the high intensity.

In the light source section 13', the laser beam emitted from the semiconductor laser 1 is collected and shaped by the spherical lens 201 of the beam shaping section 2*a*, reflected by the optical member 203, enters the beam shaping section 2*b*, and reflected by the optical member 203'. On the other hand, the laser beam emitted from the semiconductor laser 1' is collected and shaped by the spherical lens 201' of the beam shaping section 2*b*, and transmitted through the optical member 203'. The two light beams shaped in the beam shaping sections 2*a* and 2*b* and combined into one laser beam by the beam shaping section 2*b* in this manner are caused to outgo through the spherical lens 202', focused on an incident end surface of the optical fiber 3 by the fiber incident optical system 31, and outgo to the dichroic mirror 15 through the optical fiber 3, the fiber outgoing radiation optical system 32 and the lens 33.

When the two or more semiconductor light sources are required in this manner, it is possible to cope with such a case by connecting the optical systems on the radiation side like the above-described semiconductor lasers 1 and 1'. Although the conditions of the emitted beam from the semiconductor laser vary depending on wavelengths in many cases, beam shaping can be carried out with each wavelength in the beam shaping sections 2*a* and 2*b* in the above-described structure, thereby performing efficient image formation relative to the fiber 3.

When the above-described structure is adopted, even if a plurality of wavelengths are used and a wavelength range is a broad band, the light source section 13' can be incorporated into the scanning section 121' of the laser scanning/detecting system main body 12' without extremely increasing the size of the light source section 13'. Further, the outgoing beam from the optical fiber 3 can be processed as a point light source, and the light from the light source section 13' can be utilized as it is without greatly changing the laser scanning/detecting system main body 12' and the microscope section 11.

Figure 3:
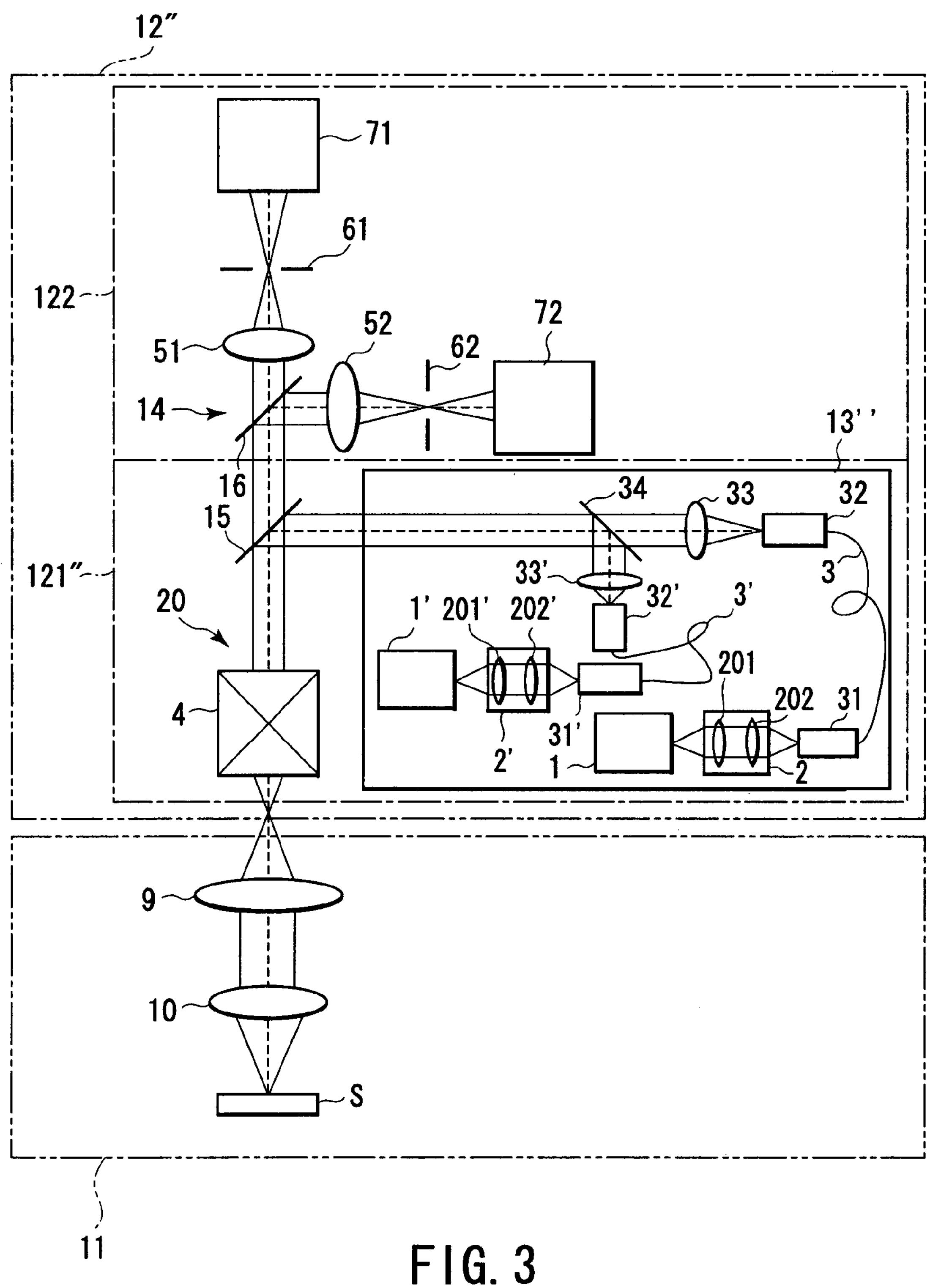
FIG. 3 is a view showing a structure of a two-channel detecting/laser scanning confocal microscope according to a third embodiment of the present invention.
Figure 4:
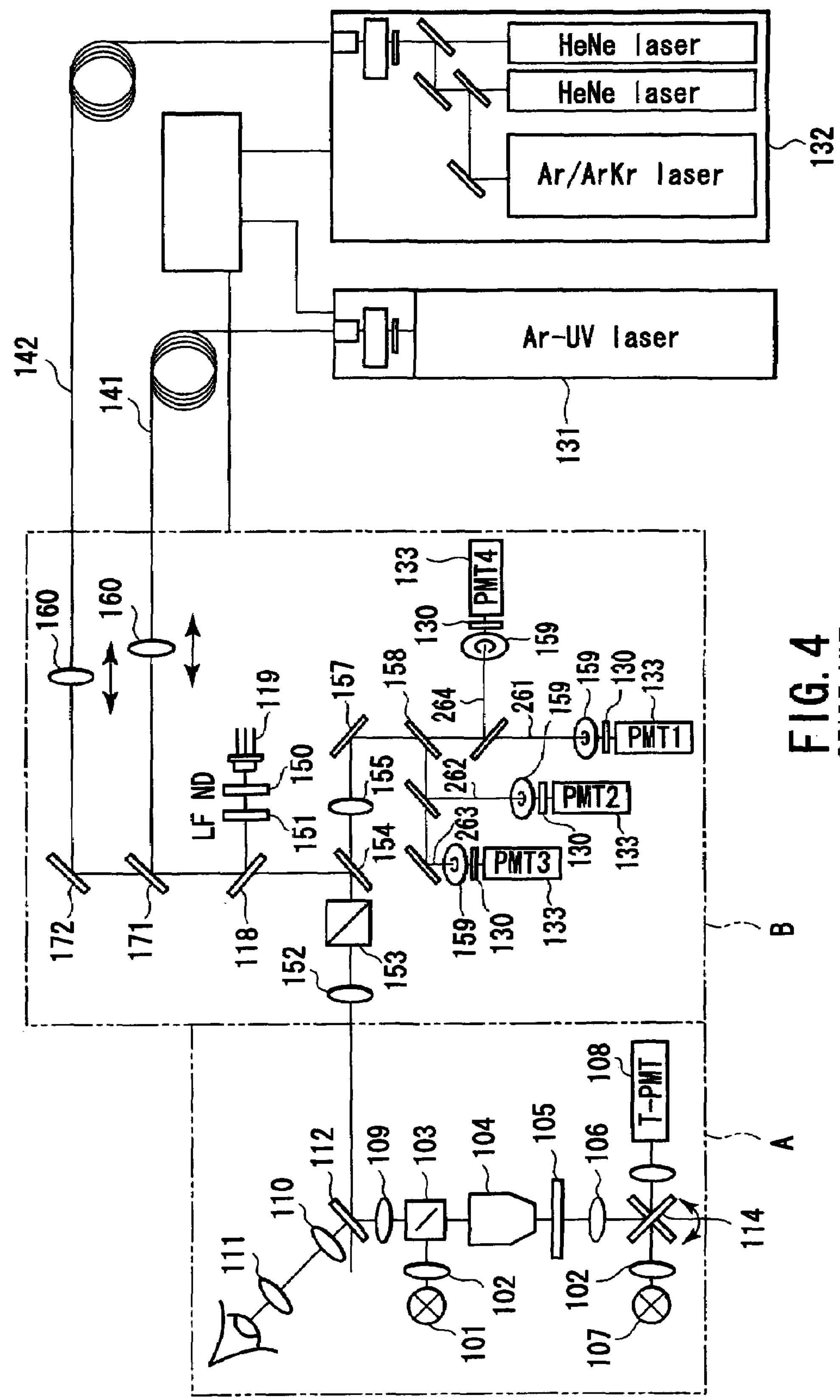
FIG. 4 is a view showing a structure of a laser microscope according to a prior art.

FIG. 3 is a view showing a structure of a two-channel detecting/laser scanning confocal microscope according to a third embodiment of the present invention. In FIG. 3, like reference numerals denote parts equal to those in FIGS. 1 and 2.

In an apparatus structure illustrated in FIG. 3, as parts different from the first and second embodiments, two types of semiconductor lasers 1 and 1' (semiconductor laser diodes: light sources manufactured by a semiconductor process) having different wavelengths are used as light sources of a light source section 13" in a scanning section 121" configuring a laser scanning/detecting system main body 12", and two beam shaping sections 2 and 2' and two types of optical fibers 3 and 3' are provided. Further, the light source section 13" comprises fiber incident optical systems 31 and 31', fiber radiation optical systems 32 and 32', lenses 33 and 33' and an optical member 34. The beam shaping section 2' has a set of spherical lenses 201' and 202.

When the semiconductor lasers 1 and 1' have different wavelengths, a dichroic mirror is used as the optical member 34. This dichroic mirror has a characteristic of transmitting a wavelength of the light from the semiconductor laser 1 and reflecting a wavelength of the light from the semiconductor laser 1'. In case of equalizing the wavelengths of the semiconductor lasers 1 and 1' and improving the intensity of the light, a polarized beam splitter (PBS) is used as the optical member 34. In this case, since the laser beam outputted from each of the semiconductor lasers 1 and 1' is the linear polarized light, polarization directions of the semiconductor lasers 1 and 1' are shifted 90 degrees so as to be orthogonal to each other, and the optical member 34 is arranged so as to transmit the emitted light from the semiconductor laser 1 and reflect the emitted light from the semiconductor laser 1'. Furthermore, in this case, polarization plane preserving fibers are used as the optical fibers 3 and 3'. A use of the two semiconductor lasers having the same wavelength is very effective in cases where the output intensity should be increased and a sample should be irradiated with the beam with the high intensity.

In the light source section 13", the laser beam emitted from the semiconductor laser 1 is collected and shaped by the spherical lenses 201 and 202 of the beam shaping section 2. The shaped beam is focused on an incident end surface of the optical fiber 3 by the fiber incident optical system 31, transmitted through the optical member 34 via the optical fiber 3, the fiber radiation optical system 32 and the lens 33, and caused to outgo to the dichroic mirror 15. On the other hand, the laser beam emitted from the semiconductor laser 1' is collected and shaped by the spherical lenses 201' and 202' of the beam shaping section 2'. The shaped beam is focused on an incident end surface of the optical fiber 3' by the fiber incident optical system 31', reflected by the optical member 34 through the optical fiber 3', the fiber radiation optical system 32' and the lens 33', and caused to outgo to the dichroic mirror 15. The two light beams shaped by the beam shaping sections 2 and 2' and combined into one laser beam by the optical member 34 in this manner are caused to outgo to the dichroic mirror 15.

When the two semiconductor light sources are required as described above, the beam shaping sections 2 and 2' and the optical fibers 3 and 3' corresponding to the respective light sources are provided like the semiconductor lasers 1 and 1' mentioned above, and the light beams outgoing from the respective optical fibers 3 and 3' are combined by using the optical member 34 such as a dichroic mirror or a half mirror whose reflection and transmission are controlled. Furthermore, when three or more semiconductor light sources are required, it is possible to cope with such a case by connecting the optical systems on the radiation side like the above-described semiconductor lasers 1 and 1'.

In case of using a plurality of light sources having different wavelengths, dedicated beam shaping optical systems or optical fibers must be used depending on their bands. The above-described apparatus structure can be applied in such a case, and it is very effective when, e.g., using the ultraviolet light or near infrared light is used as a second light source.

When the above-described structure is adopted, even if a plurality of wavelengths are used and a wavelength range is a broad band, the light source section 13" can be incorporated into the scanning section 121" of the laser scanning/detecting system main body 12" without greatly changing the light source section 13". Moreover, the outgoing beams from the respective optical fibers 3 and 3' can be relatively easily combined as one and the obtained light can be used as an ideal point light source. Additionally, the light from the light source section 13" can be utilized as it is without greatly changing the laser scanning/detecting system main body 12" and the microscope section 11.

Further, the foregoing embodiments can be modified as follows.

In case of using a laser light source having a wavelength which is not provided in the light source section incorporated in the laser scanning/detecting system main body 12, the light from the laser light source is combined in a parallel light flux on the radiation side of the optical fiber 3. As a result, an available wavelength range is greatly enlarged.

According to the foregoing embodiments, the semiconductor laser (semiconductor light source) and the optical fiber are combined, and they are incorporated as the light source section in the laser scanning confocal microscope. Furthermore, a plurality of the semiconductor lasers and optical fibers may be provided based on the physical characteristic of the light. The optical fiber is a single mode fiber, and a use of a polarization plane preserving fiber enables the ideal point light source shaping, and the feature of the polarization state of the semiconductor laser can be utilized for any other illumination or a detection method in the apparatus.

Furthermore, by incorporating the above-described semiconductor light source, the optical system which shapes the light from the light source and the optical fiber into the apparatus main body, the entire apparatus structure can be reduced in size, and it can be utilized as an ideal point light source which is demanded in the laser scanning confocal microscope. Moreover, by utilizing the optical fiber, a role as a spatial filter of the optical system can be provided, thereby obtaining the ideal point light source. Additionally, when the optical fiber is used as the spatial filter, the radiation end of the optical fiber can be freely set as different from the conventional pin hole method, and a degree of freedom can be provided in arrangement of the optical system in the apparatus.

Further, even when a plurality of the semiconductor lasers are used and their wavelengths are different from each other, if they are so-called visible light band, they can be combined as one light flux in the optical system which shapes the light from the light source and coupled to one fiber. Furthermore, when using wavelengths in the ultraviolet and near infrared light regions and the visible light regions are used, a plurality of fibers can be used in accordance with a wavelength band or a frequency band, and the wavelengths can be combined as one light flux in the apparatus main body.

In the laser scanning confocal microscope, it is preferable that the point light source to be used is as small as possible, and a use of the single mode fiber as the optical fiber can sufficiently satisfy the desired performance. On the other hand, although the linear polarized light is emitted from the semiconductor laser, the characteristic can be preserved in the optical system by using the polarization plane preserving fiber, thereby creating an efficient setup of the optical system. Moreover, by saving this characteristic, illumination and detection depending on polarization can be performed in fluorescence observation/transmission observation.

According to the present invention, the following effects can be demonstrated.

(1) According to the laser scanning microscope of the present invention, the entire apparatus can be reduced in size by incorporating the semiconductor light source and the optical fiber into the scanning optical system main body, and the ideal point light source with no astigmatic difference which can be applied to the apparatus can be created by using the outgoing light from the optical fiber.

(2) According to the laser scanning microscope of the present invention, the scanning section having the light source and the scanning optical system and the detection section which detects the light from a sample can be integrally constructed as the scanning optical system main body.

(3) According to the laser scanning microscope of the present invention, a plurality of the semiconductor light sources having different wavelengths can be used, and minimization of the apparatus can be maintained.

(4) According to the laser scanning microscope of the present invention, a plurality of the light sources can be used in a wide wavelength band of the ultraviolet region to the near infrared region. In particular, even if the dedicated beam shaping optical system and optical fiber are required, the light can be readily combined in the apparatus.

(5) According to the laser scanning microscope of the present invention, selection of the wavelength and minimization of the light source and the apparatus are enabled.

(6) According to the laser scanning microscope of the present invention, the ideal point light source can be obtained.

(7) According to the laser scanning microscope of the present invention, the linear polarization characteristic of the light source can be maintained in the apparatus.

(8) According to the semiconductor laser light source unit of the present invention, the divergent beam having an astigmatic difference component from the semiconductor laser can be condensed without omission and led to the optical fiber by shaping the condensed beam by the beam shaping section and then focusing it on the fiber end surface by the fiber incident optical system.

Since the astigmatic difference component of the beam shape which has not been completely shaped in the beam shaping section is eliminated by transmission through the optical fiber, the light outgoing from the fiber radiation end becomes a substantially ideal point light source. This is collimated by the fiber radiation optical system and converted into a parallel beam having a predetermined beam width. Therefore, even the light source unit using the semiconductor laser can efficiently obtain the parallel beam with the ideal shape which can be used in the laser scanning microscope. Further, since the semiconductor laser is used, the light source unit can be minimized.

(9) According to the semiconductor laser light source unit of the present invention, since the fiber incident optical system has a function of beam shaping and a function of condensing the light onto the fiber end surface, the optical system can be reduced in size.

(10) According to the scanning unit for the laser scanning microscope of the present invention, since the highly accurate parallel beam from the semiconductor laser light source unit can be led to the scanning optical system as it is, the small and efficient scanning unit can be realized.

(11) According to the semiconductor laser light source unit of the present invention, since a plurality of the laser beams are shaped by the respective shaping optical systems, they can be efficiently led to the optical fiber by matching the shaping optical systems to the characteristics of the individual laser beams. Since the laser beams are led to one optical fiber, a plurality of the laser beams can be combined into one beam without displacement.

(12) According to the semiconductor laser light source unit of the present invention, it is possible to generate a laser beam having the intensity corresponding to two semiconductor lasers.

(13) According to the semiconductor laser light source unit of the present invention, since the lights having different wavelengths are combined in the light source unit and the combined light is led to one fiber, it is possible to generate the laser beam including a plurality of wavelengths.

(14) According to the semiconductor laser light source unit of the present invention, since a plurality of the laser beams are shaped by the respective shaping optical systems, they can be efficiently led to the optical fiber by matching the shaping optical systems to the characteristics of the individual laser beams. Since there are respective optical fibers in accordance with individual laser beams, it is possible to use an optical fiber according to the characteristic of each laser beam.

That is, according to the present invention, it is possible to provide the laser scanning microscope which uses the semiconductor light source and intends a reduction in size of the apparatus and maintenance of the image quality, semiconductor laser light source unit, scanning unit for a laser scanning microscope, and a method of connecting the semiconductor light source to the scanning microscope. Therefore, the light source section can be integrated into the apparatus, and the entire apparatus can be reduced in size.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A laser scanning microscope comprising:

a light source section which emits a laser beam; and a scanning optical system which scans the laser beam from the light source section on a sample;

wherein the light source section comprises a first semiconductor laser diode and a first optical fiber which leads the laser beam from the semiconductor laser diode to the scanning optical system; and wherein the light source section and the scanning optical system are provided in one housing.

2. The laser scanning microscope according to claim 1, wherein the optical fiber comprises a single mode optical fiber.

3. The laser scanning microscope according to claim 1, wherein the optical fiber comprises a polarization plane preserving type optical fiber.

4. The laser scanning microscope according to claim 1, wherein the light source section further comprises:

a beam shaping section which condenses the laser beam emitted from the semiconductor laser diode and shapes a beam form thereof;

a fiber incident optical system which focuses the laser beam outgoing from the beam shaping section on an incident end surface of the optical fiber; and a fiber radiation optical system which collimates the laser beam outgoing from the optical fiber.

5. The laser scanning microscope according to claim 1, wherein the light source section further comprises:

at least a second semiconductor laser diode; and a combining optical system which combines laser beams emitted from the semiconductor laser diodes into one laser beam; and wherein the laser beam led by the optical fiber is the laser beam combined by the combining optical system.

6. The laser scanning microscope according to claim 5, wherein the combining optical system comprises a polarized beam splitter.

7. The laser scanning microscope according to claim 5, wherein the combining optical system comprises a dichroic mirror.

8. The laser scanning microscope according to claim 5, wherein the light source section further comprises:

a first beam shaping section which condenses the laser beam emitted from the first semiconductor laser diode and shapes a beam form thereof; and a second beam shaping section which condenses the laser beam emitted from the second semiconductor laser diode and shapes a beam form thereof;

wherein the first beam shaping section includes the combining optical system, and the combining optical system combines the laser beam in the first beam shaping section and the laser beam outgoing from the second beam shaping section.

9. The laser scanning microscope according to claim 5, wherein the semiconductor laser diodes emit visible light band lasers.

10. The laser scanning microscope according to claim 1, wherein the light source section further comprises:

at least a second semiconductor laser diode;

a second optical fiber; and a combining optical system which combines a plurality of laser beams outgoing from the optical fibers into one laser beam.

11. The laser scanning microscope according to claim 10, wherein the combining optical system comprises a polarized beam splitter.

12. The laser scanning microscope according to claim 10, wherein the combining optical system comprises a dichroic mirror.

13. The laser scanning microscope according to claim 10, wherein the light source section further comprises:

a first beam shaping section which condenses a laser beam emitted from the first semiconductor laser diode and shapes a beam form thereof;

a second beam shaping section which condenses a laser beam emitted from the second semiconductor laser diode and shapes a beam form thereof;

wherein the first optical fiber leads the laser beam emitted from the first beam shaping section, and the second optical fiber leads the laser beam emitted from the second beam shaping section.

14. The laser scanning microscope according to claim 10, wherein the semiconductor laser diodes emit laser light including at least one of an ultraviolet light, a near infrared light and a visible light.

* * * * *